United States Patent [19]

Meetze, Jr.

[11] 4,432,938

[45] Feb. 21, 1984

[54] APPARATUS FOR CREATING A FLOW OF AIR PAST A PRODUCT CAPABLE OF BEING VAPORIZED

[75] Inventor: Murray O. Meetze, Jr., Columbia, S.C.

[73] Assignee: Risdon Enterprises, Inc., Columbia, S.C.

[21] Appl. No.: 259,070

[22] Filed: Apr. 30, 1981

[51] Int. Cl.³ .............................................. A61L 9/12
[52] U.S. Cl. ...................... 422/49; 261/95; 261/101; 261/DIG. 17; 261/DIG. 65; 422/124; 422/306
[58] Field of Search ......... 261/95, 101, 102, DIG. 17, 261/DIG. 65; 422/49, 124, 305, 306; 239/56, 60

[56] References Cited

U.S. PATENT DOCUMENTS

| | | | |
|---|---|---|---|
| 1,254,337 | 1/1918 | Marsh | 422/124 |
| 3,990,848 | 11/1976 | Corris | 422/124 |
| 3,993,444 | 11/1976 | Brown | 261/DIG. 17 |
| 4,035,451 | 7/1977 | Tringali | 261/101 |
| 4,059,422 | 11/1977 | Steiner | 261/DIG. 17 |
| 4,111,655 | 9/1978 | Quincey | 422/124 |
| 4,154,251 | 5/1979 | Doyel | 422/124 |
| 4,166,087 | 8/1979 | Cline et al. | 261/DIG. 17 |
| 4,272,261 | 6/1981 | Lynch, Jr. et al. | 422/124 |
| 4,294,778 | 10/1981 | DeLuca | 261/DIG. 65 |
| 4,301,095 | 11/1981 | Mettler et al. | 261/102 |

Primary Examiner—Barry S. Richman
Attorney, Agent, or Firm—St. Onge, Steward, Johnston & Reens

[57] ABSTRACT

The disclosed battery-powered vapor dispensing apparatus has a housing with an access opening, an air intake port, an air discharge port, and means for supporting a vaporizable product in a path between the intake and discharge ports. A structurally-integrated mechanism for creating air flow along the path, assembles as a unit with the housing. The mechanism includes a chassis and an electric motor having electrical contact lugs on one end and a shaft supporting a fan projecting from the other. The chassis comprises a base, means for mounting the motor, a battery compartment, and means for mounting two resilient wire connectors such that one portion of each is resiliently urged against a lug of the motor and a second portion of each is resiliently urged against a battery terminal. The chassis fits within the access opening such that the motor, fan, connectors, and battery compartment are positioned on one side of the base, and the opposite side of the base constitutes a generally continuous extension of the housing exterior.

17 Claims, 7 Drawing Figures

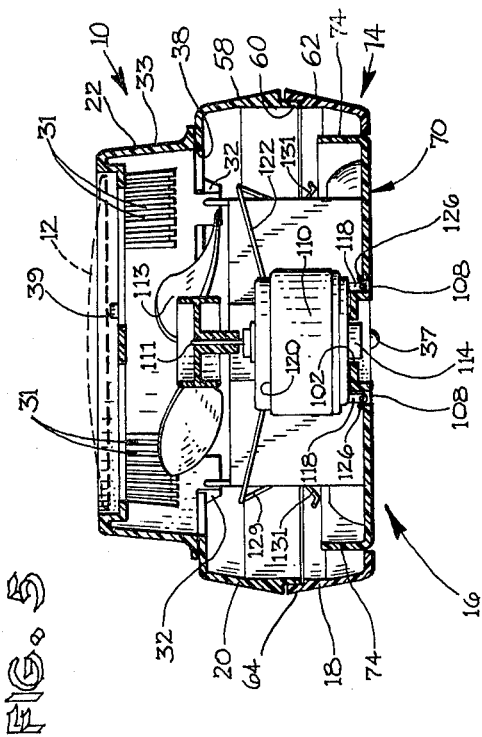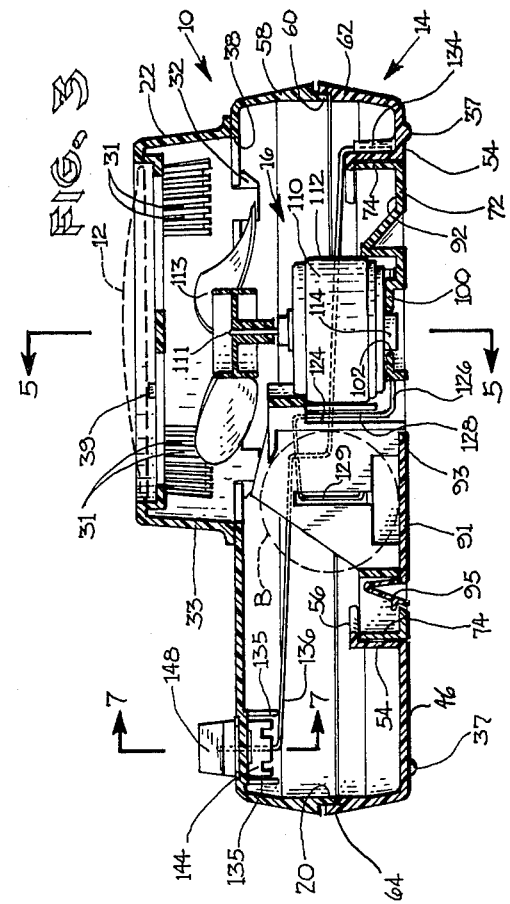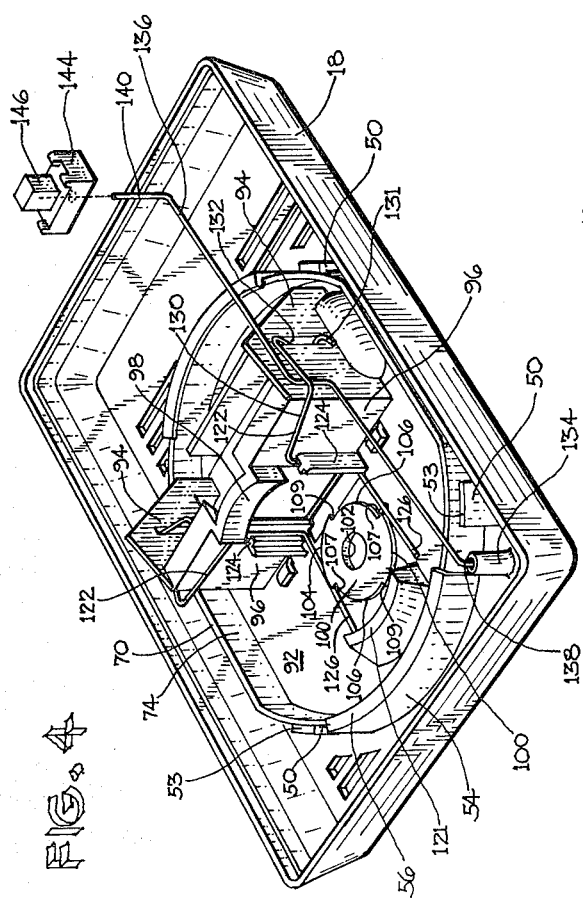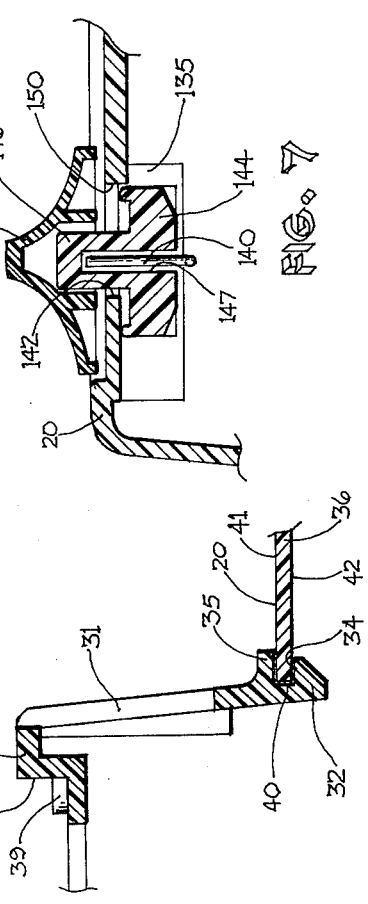

APPARATUS FOR CREATING A FLOW OF AIR PAST A PRODUCT CAPABLE OF BEING VAPORIZED

BACKGROUND OF THE INVENTION

1. Field of the Invention

The present invention relates to an improved apparatus for creating a flow of air past a product that may be vaporized in order to aid distribution of the product into the environment. More particularly, the present invention relates to a mechanism that includes the main operating components of the apparatus, which may be easily and conveniently assembled with housing structures of various exterior designs. Accordingly, maximum flexibility for design of devices for different needs and different applications is provided.

Many volatile products are desirably distributed relatively uniform in an enclosed space so that most efficient use of such products can be made. For example, room deodorizers, insecticides, germicides, and the like function most effectively when they are distributed uniformly in all areas of the room in which they are dispensed. Accordingly, devices have been proposed for creating a flow of air over the product capable of being vaporized to aid such uniform distribution.

2. Description of the Prior Art

U.S. patent application, Ser. Nos. 012,793 (Sullivan et al.), now U.S. Pat. No. 271,092 and 117,827 (Sullivan et al.) now U.S. Pat. No. 4,276,236, both assigned to the assignee of the present invention, disclose an apparatus for inducing air flow over a product capable of being vaporized.

The apparatus includes a housing constructed to provide convenient access to the housing interior. A motor, a fan, and a specially formed battery contact are mounted in fixed position within a portion of the housing. A cartridge, which includes a battery and holds the volatile product, is insertable into the housing in such a manner that the terminals of the battery make electrical connection with the battery contact mounted in the housing to link the battery to the electric motor. The motor and fan are located in the housing and relative to the mounted cartridge so that air flow passes through air intake openings, along a path through the cartridge, past the product capable of being vaporized, and then back out of the housing through air discharge openings.

U.S. Pat. No. 4,035,451 (Tringali), also assigned to the assignee of the present invention, discloses a similar apparatus and a specific structure for the cartridge that includes the battery and the product capable of being vaporized.

In each of the applications and patents mentioned above, the electric motor, fan, and battery contacts for linking the fan to the battery are designed for efficient placement in fixed position within a housing structure of a particular design or form. That is, the housing structure in each is generally cylindrical and the internal components are arranged to create a flow of air axially through the housing past the product. However, in different applications, different housing designs may be desirable. For example, a system to be used on table tops in residences may desirably utilize a housing having a relatively low, unobtrusive profile. An apparatus to be used in institutional applications may be wall-mounted, larger and have different aesthetic requirements. However, for manufacturing purposes, it is most economical to standardize components for use in apparatus for various applications so that special redesign of the internal components for particular applications is unnecessary.

SUMMARY OF THE INVENTION

It is an object of the present invention to provide an improved apparatus, for creating a flow of air past a product capable of being vaporized, that includes a mechanism made as an integrated structure and comprising the main operating components of the apparatus. The integrated structure may be assembled as a unit with exterior housings of various designs.

It is another object of the present invention to provide an improved apparatus, components of which may be made and assembled quickly and economically.

It is a further object of the present invention to provide an improved apparatus that includes a mechanism made as an integrated structure which is compact and the components of which may be assembled with a minimum of steps. A further function of the integrated structure is formation of a portion of the housing in which it is mounted.

It is still another object of the present invention to eliminate expensive assembly steps such as soldering of electrical connections and to avoid use of expensive components such as commercially available switch mechanisms.

In general accordance with the present invention, the improved apparatus is powered by a battery having one terminal at each of its axially opposed ends. The apparatus includes a housing that comprises a plurality of exterior walls, which define the exterior shape and appearance of the apparatus, and an enclosed interior space. The walls are formed with an access opening into the enclosed space and with an air intake port and an air discharge port between which is defined a path for flow of air. The housing also includes a support for positioning the product in the path.

A mechanism for creating air flow along the path is made as an integrated structure for assembly as a unit with the housing. The mechanism includes a direct current electric motor having two electrical contact lugs projecting from one of its ends and a rotary shaft projecting from the opposite end. A fan is mounted on the shaft to be driven by the motor. Two resilient wire connectors are provided, each for connecting one lug of the motor to one terminal of the battery. The mechanism also includes a chassis comprising a base, a locating boss and restraining rail for mounting the motor on the chassis with the contact lugs in fixed position relative to one side of the base, a pair of partitions standing upwardly from the one side of the base and spaced by a distance slightly larger than the distance between the terminals of the battery to thereby define a battery compartment, and a pair of retainers for mounting each wire connector with one portion of it urged against one lug of the motor and a second portion of it urged to a location in the battery compartment for contacting one terminal of the battery.

The chassis is shaped and dimensioned to be received in the access opening of the housing with the side of the base opposite the one side constituting a generally continuous extension of the exterior walls. Further, with the chassis so received in the access opening, the motor, the fan, the connectors, and the battery compartment are positioned within the enclosed space and the fan is located to create air flow along the path.

The motor, chassis, and resilient wire connectors, are all constructed so that the connectors may be snapped into and held in place on the chassis and the motor may be snapped and rotated into and held in place to bring the one portion of each connector into contact with one of the respective lugs of the motor. Accordingly, soldered connections between the connectors and motor lugs are unnecessary. Therefore, assembly of the motor and connectors is made easier by elimination of soldering steps and may be accomplished more efficiently and economically.

The housing and chassis are also formed with special snap fitting interengaging mounts that permit the chassis to be easily assembled in the access opening of the housing.

Accordingly, significant improvements are provided by the apparatus of the present invention in both ease of manufacture and assembly and in the versatility with which its various components may be used.

These and other objects, aspects, and features of the present invention will be pointed out in or will be understood from the following detailed description provided in conjunction with the accompanying drawings.

BRIEF DESCRIPTION OF THE DRAWINGS

FIG. 3 is a vertical cross-sectional view of the assembled apparatus taken through plane 3—3 in FIG. 1.

FIG. 4 is a perspective view of the bottom section of the housing assembled with the chassis, but with the motor and fan removed to show details of the chassis. The view is seen from the top and rear-left.

FIG. 5 is a vertical cross-sectional view taken through plane 5—5 in FIG. 3 showing the positions of one portion of each wire connector in contact with one motor lug.

FIG. 6 is a partial vertical cross-sectional view taken through plane 6—6 in FIG. 1 showing the attachment of two upper components of the housing.

FIG. 7 is a vertical cross-sectional view taken through the plane 7—7 in FIG. 3 showing a switch mechanism for interrupting current flow to the motor from the battery.

DETAILED DESCRIPTION OF THE PREFERRED EMBODIMENT

Figure 1:
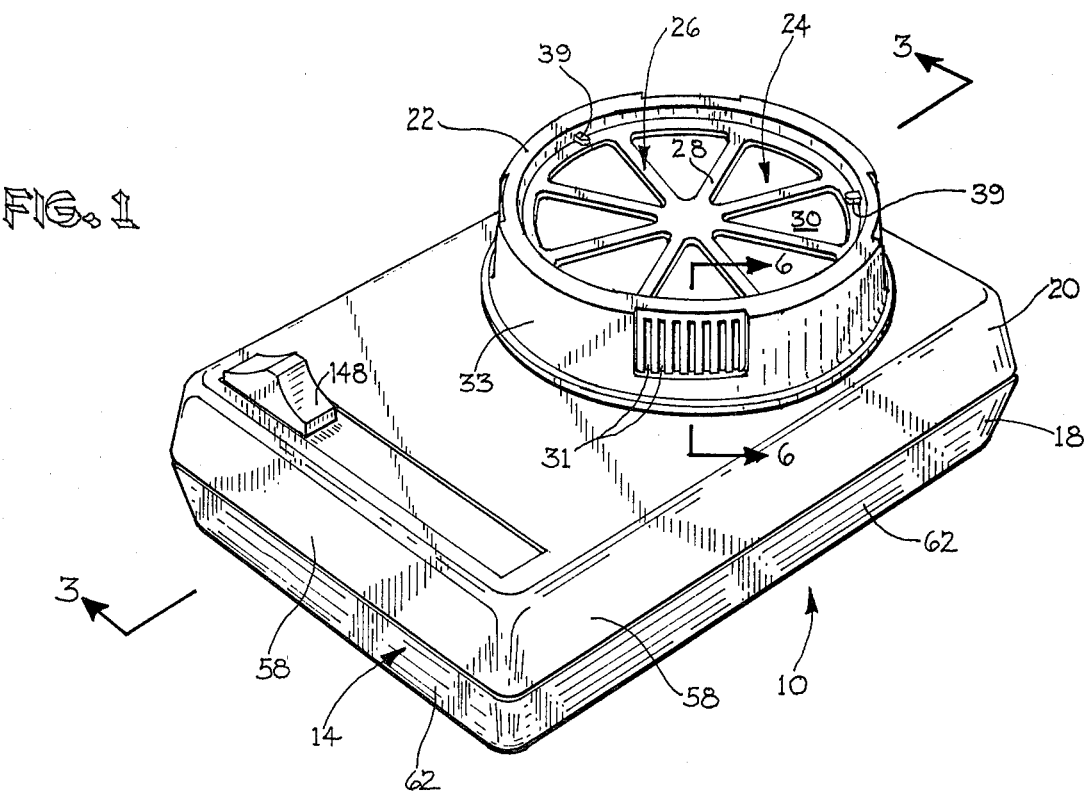
FIG. 1 is a perspective view of the apparatus of the present invention for creating a flow of air past a product capable of being vaporized.

FIG. 1 illustrates the improved apparatus in accordance with the present invention, generally indicated at 10, which is designed to induce a flow of air over or past a product capable of being vaporized. In the preferred embodiment, this apparatus is specifically designed for use with a device, such as that disclosed in U.S. Pat. No. 4,094,119 (Sullivan), that holds the product for release through a permeable membrane. This device, generally indicated in FIGS. 3 and 5 at 12 by phantom lines, is thin or sheet-like and comprises a number of layers of polymeric material heat welded together about a closed boundary to confine the product therein. One of the layers is microporous or ultramicroporus to permit the product to migrate therethrough to then volatilize into the environment. In the preferred embodiment of the present invention, this device is round or disc-shaped in plan view. However, other shapes are satisfactory for purposes of this invention. It will also be appreciated that other packages for the volatile product may also be devised or the product may be supported in a manner described below independently of any package.

The apparatus of the present invention supports the device 12 and, hence, the product and includes components for creating a flow of air past or against the device to distribute the volatile product into the environment in which the apparatus is placed. More particularly, the apparatus includes a housing, generally indicated at 14, and a mechanism, generally indicated at 16, for creating the flow of air through the housing past the product. The housing provides the exterior appearance of the apparatus as well as a support for the product so that it may be mounted in a path along which a flow of air is created. The mechanism 16 includes the main operating components of the apparatus. It is made as a unitary structure and is adapted to be snap-fitted as a unit into the housing for easy and convenient assembly. Accordingly, the housing may have any of a number of external configurations depending upon the application for the apparatus, while the mechanism 16 has a "universal" configuration for easy assembly with the housing regardless of its general exterior configuration.

Figure 2:
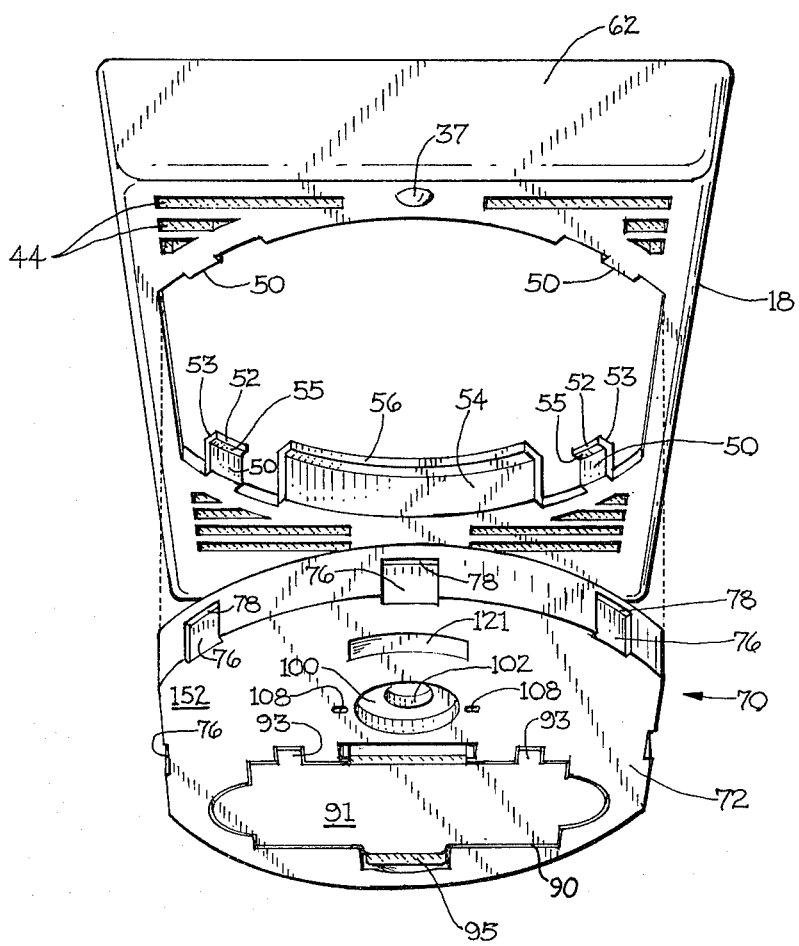
FIG. 2 is an exploded perspective view of a bottom section of a housing and of a chassis positioned for assembly with this section. The view is seen from the bottom and front of both components.

As shown in greater detail in FIGS. 2, 3 and 4, the housing includes a lower housing section 18, an upper housing section 20, and a housing chimney 22. In the preferred embodiment, the lower and upper housing sections are assembled to form a generally rectangular structure in plan view having a relatively low height or profile. The upper and lower housings together define a structure approximately the same size as a conventional table-top calculator or cassette tape recorderplayer and may be positioned on a table top or other horizontal surface. The design is clean, unobtrusive and esthetically pleasing.

The chimney section 22 is generally cylindrical and includes an upper open end 24 and a web 26 of spokes 28 that each span the open end. The web obstructs access of foreign objects into the interior of the housing yet defines several openings 30 through which air may nevertheless pass to flow against the device 12 in a manner described in greater detail below. The chimney section is also formed with a plurality of air discharge ports 31 in its side exterior wall 33.

The open end 24 of the chimney 22 is shaped and dimensioned to receive the device 12 holding the volatile product as shown in FIGS. 3 and 5. Three small ribs 39 project radially inwardly in the open end 24 and are spaced above web 26 to support the device 12 at its edge in the open end 24. Further, the device can be removed from the open end 24 for replacement by being pressed downwardly at a portion of its edge at a location between two ribs 39 to tilt an opposite portion of the edge of the device upwardly so that it can be grasped.

As can be seen in FIGS. 3, 5 and 6, at its lower edge 29, the chimney section 22 is formed with four depending snap fingers 32 each formed with a radially outwardly projecting flange surface 34. The upper wall 36 of the upper housing section 20 is formed with a hole 38 having four notches 40 in its periphery, each corresponding to one of the snap fingers 32 on the chimney section. A radially outwardly extending flange 36 is also formed at the lower edge 29 of the chimney section and is axially spaced above the flange surface of each snap finger. The chimney section is assembled with the upper housing section by snapping the fingers 32 into the hole, with each finger registered with one notch 40, until the flange 35 contacts the upper surface 41 of the upper housing section upper wall and the flange surface 34 snaps under the undersurface 42 of the upper wall 36.

The upper housing section further includes four depending peripheral side walls 58 that terminate in a peripheral bonding rib 60. Similarly, the lower housing section 18 is formed with four upstanding peripheral side walls 62 formed on their inner surfaces at their upper extremes with a peripheral bonding rabbet 64 that is shaped and dimensioned to interfit with the bonding rib. The upper and lower housings are assembled by applying a solvent bonding compound to the bonding rib 60 of the upper housing and inserting it into the bonding rabbet 64 of the lower housing section. When the upper and lower sections are so assembled and the chimney section 22 is mounted in the hole 38 of the upper section, the assembled structure defines an enclosed interior space in which the operative components of the apparatus are mounted in a manner described below.

As shown in FIG. 2, the lower housing section 18 is formed with a plurality of air intake ports 44. A path for flow of air is defined between these intake ports 44 and the discharge ports 31 in the chimney 22. The lower housing section also has three feet 37 formed on its bottom wall 46 that space this wall slightly above a surface on which the apparatus is supported. In this way, air may flow under the bottom wall into the intake ports 44.

Accordingly, air flow can be created along the path between the intake and discharge ports may pass through the openings 30, impact the bottom of the device 12, which comprises its permeable layer, and thereafter flow out of the discharge ports 31 carrying with it vapors of the volatile product.

The bottom wall 46 of the lower housing section 18 is further formed with a large access opening 48. Four snap legs 50 project upwardly from the periphery of the opening 48. Each snap leg has an inwardly projecting latch tab 52 at its upper extreme that provides an upwardly facing latch surface 53 and a downwardly, outwardly beveled cam surface 55.

A pair of guide walls 54 also project upwardly from the periphery of the access opening 48. Each guide wall is positioned between two snap legs 50 and at its upper extreme is formed with an inwardly projecting limit flange 56. The functions of the snap legs 50, guide walls 54 and limit flanges 56 will be explained in greater detail below.

Referring to FIGS. 2 and 4, the universal mechanism 16 includes a chassis 70 having a base 72 and a side wall 74 standing upwardly from the periphery of the base 72. The side wall 74 is formed with a plurality of recesses 76, each of which terminates at its upper end in a downwardly facing stop surface 78. Each of the recesses 76 is positioned in the wall 74 to receive one of the snap legs 50 projecting upwardly from the periphery of the access opening in the lower housing section by insertion of the chassis into the housing. The cam surfaces 55 aid in camming the snap fingers 50 outwardly to snap into the recess 76 during insertion. With the chassis fully received in the access opening, an upper edge of the side wall 74 abuts the limit flanges 56 of the guide walls 54 and the latch tab 52 on each snap leg 50 abuts one stop surface 78 in one recess 76. Accordingly, interengagement of the edge of the side wall 74 and limit flanges 56 prevents insertion of the chassis into the housing beyond the mounted positions (FIGS. 3, 4 and 5). Interengagement of the latch tabs 52 and stop surfaces 78 prevents demounting of the chassis from the mounted position in the housing.

The base of the chassis is further formed with a hatch opening 90 shaped and dimensioned to receive a conventional "D" size cylindrical flashlight battery B shown in phantom in FIG. 3.

A hatch door 91 is hinged at its rear 93 to the base of the chassis and is formed with a catch 95 at its front to secure it in a closed position.

At opposing ends of the hatch opening, projecting upwardly from the upper surface 92 of the base 72, are two partitions 94 which are spaced by a distance slightly larger than the axial dimension of the battery. The partitions 94 are interconnected by two rear walls 96 joined by an arcuate rail 98. The rear wall sections 96, together with the partitions 94, define a battery compartment in which a battery for powering the apparatus is received.

As can be seen in FIGS. 3 and 4, access to the battery compartment for placement of a battery therein may be had from below the chassis 70 through the hatch 90 or from the above chassis. This design feature permits maximum flexibility of the chassis as will further be described below.

The upper surface 92 of the base 72 is further formed with a cylindrical upstanding boss 100 behind the rear wall sections, that has a central cylindrical socket 102. The boss has an upstanding peripheral surface having two diametrically opposed arcuate sections 104 of large diameter and two other diametrically opposed arcuate sections 106 of smaller diameter which are interconnected by radially extending walls two of which 107 extend laterally of the chassis and two 109 of which extend longitudinally. A socket 108 through the base of the chassis is formed to define an interior wall that constitutes an extension of each wall 107. Therefore, a line passing through the sockets 108 extends generally parallel to the rear walls 96 of the battery compartment.

The mechanism further includes a direct current, low power electrical motor 110 housed in a generally right cylindrical shell 112. A cylindrical button 114 projects axially from one end 116 of the shell and a pair of contact lugs 118 project from the same end at diamtrically opposed positions relative to the button 114. The inner edges of the lugs 118 are spaced by a distance slightly larger than the diameter of small arcuate sections 106 of the boss. The outer edges of the lugs are spaced by a distance slightly larger than the diameter of large arcuate sections 104 of the boss.

Accordingly, the motor may be mounted in the chassis by placing the button 114 in the button socket 102 with the contact lugs 118 near the longitudinally extending walls 109 of boss 100. The motor may then be rotated about its axis and that of socket 102 in a clockwise direction until the contact lugs 118 register with the lug sockets 108 allowing the motor to be snapped axially downwardly with the lugs received in the socket 108. The rail 98 is also spaced upwardly from the boss and projects rearwardly sufficiently to overlie or embrace a portion of the end 120 of the motor shell opposite the one end 116 (FIG. 3). Further, a back-up rail 121 projects upwardly from the base 72 of the chassis to contact a lower portion of the motor shell and provide additional support to hold the motor in its mounted position. Accordingly, the motor is securely mounted on the chassis merely by being rotated and snapped into place within the confines of the boss, rail and back-up rail 121.

The motor also has a rotary shaft 111 that carries a low mass molded fan 113. When the motor receives electric power, it drives the fan through the shaft to create flow of air along the path.

Electrical connection is made between the contact lugs 118 of the motor and terminals of a battery received in the battery compartment by a pair of resilient wire connectors 122 each of which has a special form. More particularly, a connector channel 124 is formed on the rear surface of each rear wall 96 opposite the battery compartment to mount each connector. The wire connector is formed with a first horizontally extending portion 126 that lies adjacent one contact lug slot 108 formed in the base of the chassis. A second portion 128 extending upwardly at a right angle to the first is confined in the one channel 124. A remaining portion 130 extends laterally outwardly of the chassis from the top of the channel, longitudinally forwardly along the outer side of one partition 94 and then projects laterally back inwardly as an arcuate section 129 through a slot 132 into the battery compartment to a location to be contacted by a terminal of a battery received therein. A limiting knuckle 131 is formed at an end of the arcuate section 129 to prevent it from passing completely through slot 132.

The first portion 126 of the wire form is held by the channel 124 so that its natural resiliency urges it against the side surface of one large diameter arcuate section 104 adjacent a lug slot 108. Each such portion therefore chordially intersects an arc described by a contact lug 118 when rotated to mount the motor as described above. Accordingly, when the motor is snapped onto the chassis as described above, and is rotated to move the contact lugs 118 to positions over the lug slots 108, each lug contacts the first portion 126 of one wire connector. Because of the resiliency of the wire connectors, positive electrical connection is made with the contact lugs without the need of a soldered connection.

Accordingly, the motor, battery connectors, and chassis are easily assembled by being snapped together without need for secondary operations such as soldering. This convenience of assembly which results from the design of the components of the chassis greatly enhances the economy with which it may be made.

It will further be appreciated from the figures that the chassis, while having relatively complex shapes for forming the battery compartment and motor and wire connector mounts, may nevertheless be made with two-part, up-down molding techniques without reentrant mold sections.

As shown in FIG. 4, the apparatus of the present invention further includes an arrangement that avoids use of a conventional, commercially available switch mechanism for turning the motor on and off by opening the circuit from the battery to the motor. This arrangement includes a wire-formed lever 136 having a depending end 138 received for lateral pivoted movement in a pivot socket 134 formed at the left rear of the lower housing section. An opposing upstanding end 140 of the lever 136 projects to a position adjacent a switch opening 142 in the left forward portion of the upper housing section. Between its ends the lever 136 passes between one partition 94 and the wire connector 122. Thus, as can be seen in FIG. 4, movement of the lever to the left (right as shown in FIG. 4) pulls the wire connector out of the slot 132 and therefore out of contact with a terminal of the battery. This, of course, opens the circuit to the motor and stops the motor from rotating. Similarly, rightward movement of the lever permits the connector 122 to return under the influence of its natural resiliency to a position in which its arcuate portion 129 contacts the terminal of the battery to complete the circuit.

The lever 136 is operated from the exterior of the housing by a two-part sliding switch button that includes a lower part 144 having an upstanding finger 146 projecting through the opening 142. The finger is formed with a hole 147 that receives the upstanding end of the lever. A second upper part 148 of the botton is mounted above the upper housing and is received with a tight friction fit on the finger 146. Accordingly, lateral movement of the button laterally moves the lever as described above.

As shown in FIGS. 3 and 7, the bottom surface of the upper housing is formed with a pair of spaced parallel guide walls 135 that laterally guide the lower part 144 of the button. A longitudinally extending, leftwardly facing edge 150 is formed on the undersurface of the upper housing section to block rightward, circuit closing movement of the lower part 144 of the button and, hence, the lever. The lever is desirably made of resilient wire that urges the lower part 144 upwardly so that its rightward circuit-closing movement is blocked by the ledge 150. The switch button may be operated, however, to close the circuit by such rightward movement by pressing the upper part 148 downwardly to move the lower part 144 out of interfering engagement with the ledge. The resiliency of the wire connector 122 operated on by the lever is also sufficient to close the circuit when the lower button part is so released. Mechanical devices oher than the lever 136 described above, may be provided to move one connector 122 out of contact with one terminal of a battery in order to open the circuit to the motor.

From the detailed description provided above, it can be seen that the mechanism 16 for the apparatus of the invention may be adapted to any housing structure which has a similar attachment arrangement such as the snap legs 50 and guide walls 54 since the shape of the access opening does not depend upon the shape of the exterior of the housing. Therefore, the housing may have various designs and still use the universal chassis mechanism in accordance with the invention.

Further, the surface 152 of the base 72 opposite the one surface 92 forms a continuous extension of the lower wall 46 of the lower housing structure. When the chassis is mounted in the access opening as described above, the motor, battery compartment, battery connector and fan are mounted in the enclosed space to be concealed in the housing. Further, when the fan is operated, air is drawn in through the intake ports through the housing to the discharge ports along the path. This air flow first impacts on the bottom of the device 12 for the product capable of being vaporized, through holes 30, to take vapors of the product out through the discharge ports 31. Accordingly, it will be appreciated that the apparatus of the present invention represents a substantial improvement over known apparatus.

Although a specific embodiment of the present invention has been described above in detail, this is only for purposes of illustration. Modifications may be made to the described structure in order to adapt this apparatus for creating a flow of air past a volatile product to particular applications.

What is claimed:

1. An improved apparatus, for creating a flow of air past a product capable of being vaporized, powered by a battery having one terminal at each axially opposed end thereof; said apparatus comprising:
   a housing including a plurality of exterior walls defining an enclosed interior space with an access opening into said space and further defining an air intake port, an air discharge port, and a path for flow of air between said intake and discharge ports; said housing further including means for supporting said product in said path; and
   a mechanism, for creating air flow along said path, made as an integrated structure for assembly as a unit with said housing, said structurally integral mechanism including
   (a) a direct current electric motor having two electrical contact lugs projecting from one end thereof and a rotary shaft projecting from an opposite end thereof;
   (b) a fan mounted on said shaft to be driven by said motor;
   (c) two resilient wire connectors each for connecting one lug of said motor to one terminal of a battery, the resilient characteristic of said connectors providing for effective electrical contact of said lugs to the terminals of a battery without further need for additional mechanical or soldered affixing means;
   and
   (d) a chassis comprising a base, means for mounting said motor on said base with said lugs in fixed position relative to one side of said base, a pair of partitions standing upwardly from said one side of said base and spaced by a distance slightly greater than the distance between the terminals of a battery to thereby define a battery compartment, and means for mounting each wire connector with one portion thereof resiliently urged against one lug of said motor and a second portion thereof resiliently urged to a location in said compartment for contacting one terminal of said battery; said chassis further being shaped and dimensioned to received in said access opening with the side of said base opposite said one side constituting a generally continuous extension of said exterior walls and with said motor, said fan, said connectors and said battery compartment positioned within said space and said fan located to create air flow along said path.

2. An apparatus according to claim 1 further comprising means for non-demountably snap fitting said chassis in said access opening of said housing.

3. An apparatus according to claim 1, wherein said base is formed with a hatch opening to said battery compartment shaped dimensioned to receive said battery for insertion therethrough.

4. An apparatus according to claim 1, wherein said battery compartment is open from the top and has a closable hatch at the bottom to enable insertion of a battery into said battery compartment from either said side of said base.

5. Apparatus according to claim 1, said product being confined in a rigid sheet-like package for release therefrom, said housing comprising an aperture shaped and dimensioned to receive said package, said means for supporting said product comprising a plurality of ribs projecting in coplanar relation inwardly of said aperature for supporting an edge of said package.

6. An apparatus according to claim 5, said housing further comprising a web formed to partially close said aperture and located inwardly of said ribs toward said enclosed space.

7. An apparatus according to claim 1, wherein said motor comprises an exterior shell from one end of which said contact lugs project, said shell being formed with a locating button also projecting from said one end thereof; and wherein motor mounting means comprises a button socket formed in said one side of said base to receive said locating button and a rail secured to said base and spaced from said one side of said base for embracing a portion of the end of said motor shell opposite said one end.

8. An apparatus according to claim 7, wherein said one side of said base is further formed with two lug sockets for receiving said motor contact lugs when said motor is in said mounted position.

9. An apparatus according to claim 8, wherein said button and said button socket are formed to permit rotation of said motor shell about an axis passing therethrough, wherein said contact lugs are located on opposite sides of said axis and wherein said wire connector mounting means urge said one portion of each said wire connector radially inwardly toward said axis into the region of one said lug socket to chordally intersect an arc described by movement of one said lug about said axis, whereby said motor shell may be rotated about said axis until said lugs are registered with and received in said lug sockets and each of which is contacted by said one portion of one said wire connector.

10. An apparatus according to claim 1, said housing having a plurality of legs projecting from the periphery of said access opening into said space, said chassis comprising a side wall standing upwardly from the periphery of said base, a portion of which complements each said leg, one said leg and one said complementary portion having a latch tab and the other thereof having a catch surface for engaging said latch tab to secure said chassis in the access opening of said housing in a mounted position.

11. An apparatus according to claim 10, said housing further comprising means for camming each said leg over said complementary portion of said side wall during receipt of said chassis into said access opening to interengage said latch tab and said catch surface.

12. An apparatus according to claim 11, said housing further comprising means for stopping receipt of said chassis into said access opening in said mounted position.

13. An apparatus according to claim 12, wherein said stopping means comprises a guide wall projecting from the periphery of said access opening into said space and a flange projecting laterally from an extreme of said guide wall, said side wall of said chassis abutting said flange with said chassis in said mounted position.

14. Apparatus according to claim 1, each said partition being formed with a slot therein, said second portion of each said wire connector being urged by said connector mounting means to project into one said slot into said battery compartment.

15. Apparatus according to claim 14, said second portion of each said wire connector being generally arcuate, projecting into and back out of one said slot, and including a limiting knuckle for engaging said partition to prevent said second portion from projecting through said slot.

16. Apparatus according to claim 14, further comprising switch means for breaking contact of said second portion of one of said wire connectors with one terminal of said battery.

17. Apparatus according to claim 16, said switch means comprising means accessible from said exterior walls of said housing for retracting said second portion of said one wire connector away from said one terminal.

* * * * *